United States Patent [19]
Holdren et al.

[11] Patent Number: 6,076,357
[45] Date of Patent: Jun. 20, 2000

[54] THERMOELECTRIC COLD TRAP

[75] Inventors: Michael W. Holdren, Columbus; Scott N. Danhof, Plain City; Michael J. Grassi, Worthington; Joseph A. Stets, Gahanna; G. William Keigley, Columbus, all of Ohio

[73] Assignee: Battele Memorial Institute

[21] Appl. No.: 09/216,444

[22] Filed: Dec. 18, 1998

[51] Int. Cl.[7] .................................................. F25B 21/02
[52] U.S. Cl. ........................................................ 62/3.2
[58] Field of Search ............................. 62/3.2, 3.4, 3.6

[56]  References Cited

U.S. PATENT DOCUMENTS

| | | | |
|---|---|---|---|
| 2,838,899 | 6/1958 | Lindenbald | 62/3.2 |
| 3,719,052 | 3/1973 | White | 62/3.2 |
| 4,231,256 | 11/1980 | Chapman et al. | 73/863.12 |
| 4,494,380 | 1/1985 | Cross | 62/3.2 |
| 4,730,458 | 3/1988 | Alger | 62/3.4 |
| 5,465,581 | 11/1995 | Haertl et al. | 62/50.1 |

FOREIGN PATENT DOCUMENTS

| | | | |
|---|---|---|---|
| 885-745 | 11/1981 | Japan | 62/3.2 |
| 2-176377A | 7/1990 | Japan | 62/3.2 |

*Primary Examiner*—Henry Bennett
*Assistant Examiner*—Melvin Jones
*Attorney, Agent, or Firm*—Porter, Wright, Morris & Arthur LLP

[57]  ABSTRACT

A compact, portable, thermoelectric cold trap for capturing certain gaseous species for analysis in gas chromatographs is disclosed. The U-shaped heat exchanger and T-shaped cold block for holding the adsorbent tube and heater allow the unit to operate over a temperature range from −45° to 300° C. The thermoelectric cold trap is portable and may be retrofitted to new or existing gas chromatographs. The adsorbent tube and heater are also replaceable. A method of assembling the thermoelectric cold trap and a method of operating the thermoelectric cold trap are also disclosed.

23 Claims, 15 Drawing Sheets

THERMOELECTRIC COLD TRAP

BACKGROUND OF THE INVENTION

1. Field of Invention

This invention pertains to the art of methods and apparatuses for capturing and preconcentrating certain gaseous species for analytical detection, and more specifically to methods and apparatuses for using a compact, portable thermoelectric apparatus for preconcentrating volatile organic compounds for analysis by gas chromatography.

2. Description of the Related Art

Many volatile organic compounds ("VOCs") found in ambient air are present at very low parts per billion and parts per trillion levels. To identify and quantify these compounds, researchers must employ collection techniques that preconcentrate sufficient amounts of these materials for analytical detection.

The use of cryogenic trapping to concentrate VOCs before analysis has been established as a proven technique for VOC monitoring. This method involves collecting a sample using a trap containing an inert material (e.g., glass beads) at subambient temperatures. The temperature of the trap is below the condensation temperatures for trace VOCs but above the condensation temperature for major constituents of ambient air (e.g., nitrogen and oxygen). After collection, the trap is rapidly heated, the VOCs are desorbed, and the compounds are analyzed, typically using a gas chromatographic ("GC") system.

An alternative trapping method involves the use of adsorbent materials to collect the VOCs at ambient temperatures. Popular adsorbents include Tenax-TA, silica gel, carbon molecular sieves, and activated charcoal. Desorption again is accomplished by elevating the trap temperature prior to GC analysis. Although both single adsorbent and multiple adsorbent traps are used, single adsorbent traps are unable to completely collect and/or desorb samples having a wide range of molecular weights, and may experience interference from artifacts. Multiple adsorbent traps therefore are preferred. By using selected adsorbents in a multi-bed trap configuration, collection apparatuses can be tuned to capture a wide range of compounds with minimal artifact interferences.

Typically, liquid cryogens such as nitrogen or carbon dioxide are used to cool the sample collection trap. However, large amounts of cryogen are consumed during normal operations. Use of large amounts of cryogens is costly and involves safety and logistical burdens in the handling of these materials.

Recently, several commercial GC systems have been designed to automatically preconcentrate volatile organic compounds and analyze the enriched samples. All known units, except one, make use of a liquid cryogen to facilitate operations. The non-liquid cryogenic GC system uses a thermoelectric means to cool the collection trap. However, this apparatus is an integral part of the GC system, and cannot be transferred to a different GC.

The present invention contemplates a new and improved stand-alone cold trap assembly that is simple in design, inexpensive, effective in use, and overcomes the foregoing difficulties and others while providing acceptable sample collection and preconcentration performance.

SUMMARY OF THE INVENTION

In accordance with the present invention, a new and improved stand-alone cold trap assembly is provided for use with new or existing GC systems. Sample gas at ambient temperature is passed at a specified rate for a predetermined time through a tube containing an adsorbent. The tube is received within a cold trap, which cools the tube, causing certain components of the sample gas to condense on the adsorbent present within the tube. The sample gas flow is terminated, the condensate is desorbed by heating of the tube, and the vaporized sample is directed into a gas chromatograph via a two position six-port valve.

The cold trap of the present invention achieves a target cold set point temperature of −30±5° C. and a target hot set point of 300±5° C. It is capable of heating a sample adsorbent tube from about −30° C. to about 300° C. in less than about 30 seconds and cooling the adsorbent tube from about 300° C. to about −30° C. in less than about 10 minutes. Thus, the cold trap can achieve fast cycle times and high collection and recovery efficiency of volatile analytes.

According to one aspect of the present invention, a thermoelectric cold trap for collecting a gas sample for analysis includes a U-shaped heat exchanger having a base, a thermoelectric module having a hot side and a cold side with the hot side engaging the base, a T-shaped cold block engaging the cold side of the thermoelectric module and having a cylinder for removably receiving a sample collection tube/heater assembly; and a control module electrically connected to the thermoelectric module, the control module selectively actuating the thermoelectric module to cool a sample collection tube received in the cylinder. The thermoelectric cold trap also may include a second thermoelectric module engaging the base and coupled in parallel to the first thermoelectric module. Foamed insulation is provided around the cold block.

According to another aspect of the present invention, a thermoelectric cold trap for collecting a gas sampe for analysis includes a U-shaped heat exchanger having a base, a thermoelectric module having a hot side and a cold side with the hot side engaging the base, a cold block engaging the cold side of the thermoelectric module and having a holder for removably receiving a sample collection tube containing an adsorbent, a heater communicating with a sample collection tube received in the holder, and a control module electrically connected to the heater and the thermoelectric module, the control module selectively actuating the heater and the thermoelectric module to heat and cool a sample collection tube received in the holder. The cold block may be T-shaped and the holder may be a cylinder formed integrally with the cold block. The cold block may be made from aluminum. The base, thermoelectric module, and cold block may be secured together by a clamp, such as a phenolic clamp.

The thermoelectric cold trap also may include a second thermoelectric module engaging the base. Preferably, this second module is connected in parallel to the first module. The thermoelectric cold trap further may include foamed insulation shielding the cold block. Preferably, the insulation is polyurethane foam.

The U-shaped heat exchanger preferably is finned. The heat exchanger also may include first and second side plates connected to the base and extending from opposite edges of the base.

The control module may include timing circuitry. This circuitry may set periods of hot and cold cycles and temperature controllers for controlling the temperatures of the heater and the thermoelectric module. The above-described thermoelectric cold traps may include an adapter for connecting the thermoelectric cold trap to a gas chromatograph.

In a further aspect of the present invention, an apparatus for preconcentrating gaseous species for analytical detection includes a U-shaped heat exchanger having a base, a thermoelectric module having a hot side and a cold side with the hot side engaging the base, a T-shaped cold block engaging the cold side of the thermoelectric module and having a holder for engaging a sample collection tube, a sample collection tube containing an adsorbent, with the sample collection tube being removably receivable within the holder, a heater for heating the sample collection tube received within the holder, and a control module electrically connected to the heater and the thermoelectric module, the control module selectively actuating the heater and the thermoelectric module to heat and cool the sample collection tube. The apparatus also may include a second thermoelectric module engaging the base and connected in parallel to the first thermoelectric module. Foamed insulation is provided to shield the cold block and the adsorbent tube. The control module of the apparatus may include timing circuitry for setting periods of hot and cold cycles and temperature controllers for controlling the temperatures of the heater and the thermoelectric module.

In yet another aspect of the present invention, a method of assembling a thermoelectric cold trap for collection of gas samples for analysis includes the steps of providing a U-shaped heat exchanger, fastening a thermoelectric module having a hot and a cold side to the heat exchanger with the hot side positioned against the heat exchanger; securing a cold block to the cold side of the thermoelectric module, providing a sample collection tube holder in engagement with the cold block, and electrically connecting a control module to the thermoelectric module for selectively actuating the thermoelectric module to cool a sample collection tube received in the holder.

In still another aspect of the present invention, a method of collecting volatile compounds from gas samples includes the steps of providing a U-shaped heat exchanger, fastening a thermoelectric module having a hot side and a cold side to the heat exchanger with the hot side positioned against the heat exchanger, providing a cold block having a holder for engaging a gas sample collection tube, securing the cold block to the cold side of the thermoelectric module, inserting a gas sample collection tube containing an adsorbent within the holder, providing a heater in communication with the sample collection tube, electrically connecting a control module to the thermoelectric module and the heater, passing a gas sample through the adsorbent tube received within the holder, causing the control module to actuate the thermoelectric module to cool the adsorbent tube and condense sample components, and causing the control module to actuate the heater to desorb the condensed sample components.

The present invention offers numerous advantages. The unit is portable and may be retrofitted to an existing gas chromatograph or installed in a new gas chromatograph. The T-shaped cold block minimizes heat losses, minimizes volume, increases speed of cooling of the unit, and prevents high heat fluxes to the base and thermoelectric modules. The use of foamed insulation reduces heat losses within the unit and assists in maintaining the cold trap components in their desired positions within the shell formed by the U-shaped heat exchanger. The unit offers fast cycle times and high collection and recovery efficiency of volatile compounds.

Still other benefits and advantages of the invention will become apparent to those skilled in the art to which it pertains upon a reading and understanding of the following detailed specification.

BRIEF DESCRIPTION OF THE DRAWINGS

The invention may take physical form in certain parts and arrangement of parts, a preferred embodiment of which will be described in detail in this specification and illustrated in the accompanying drawings which form a part hereof and wherein.

DESCRIPTION OF THE PREFERRED EMBODIMENT

Figure 1:
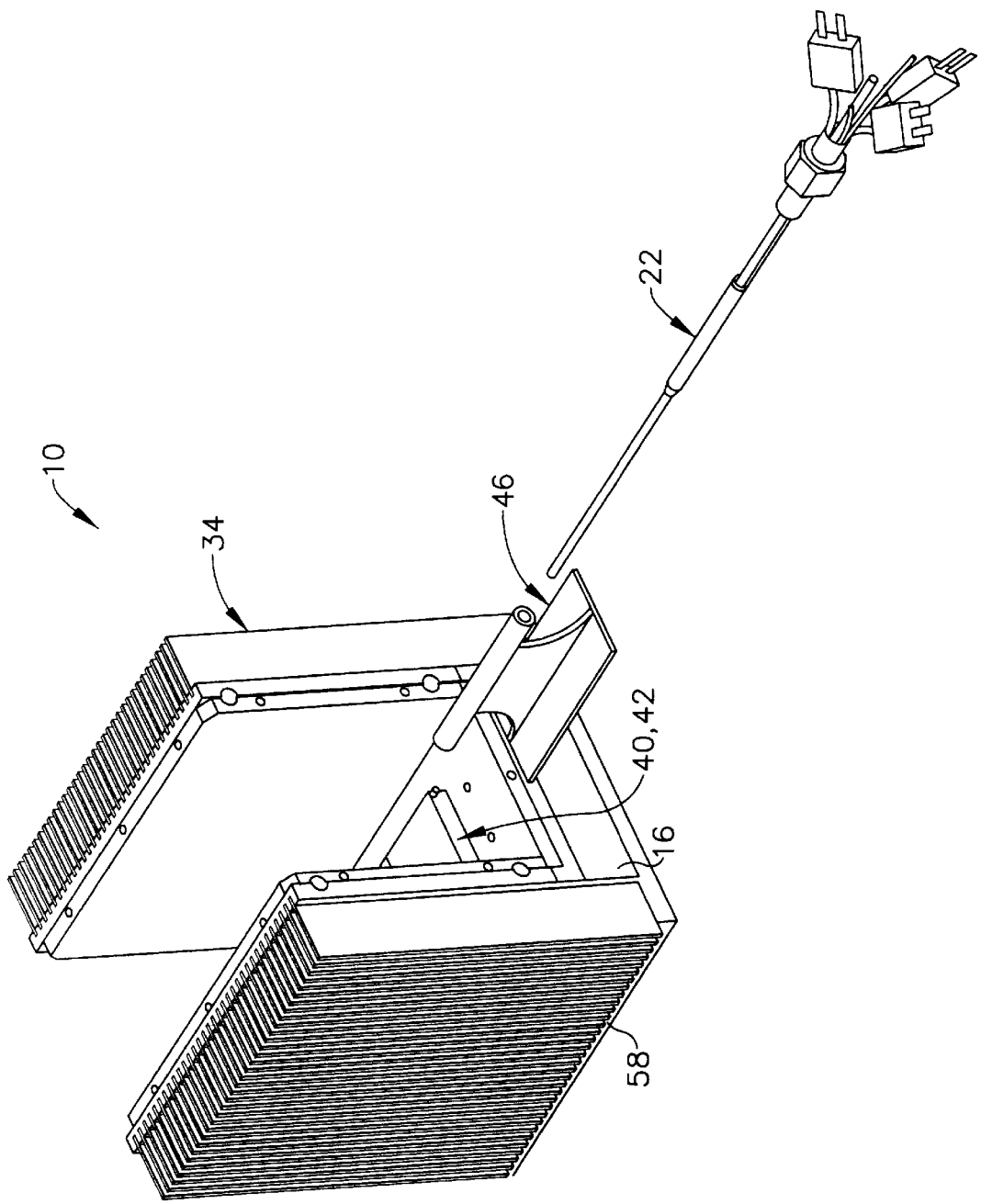
FIG. 1 shows an exploded perspective view of a thermoelectric cold trap.

Referring now to the drawings, which are provided only for the purpose of illustrating a preferred embodiment of the invention and not for limiting the invention, FIG. 1 shows a perspective view of a thermoelectric cold trap 10. The cold trap 10 is used to preconcentrate sufficient amounts of volatile organic compounds ("VOCs") found in ambient air or other gaseous media for analytical detection.

Figure 4A:
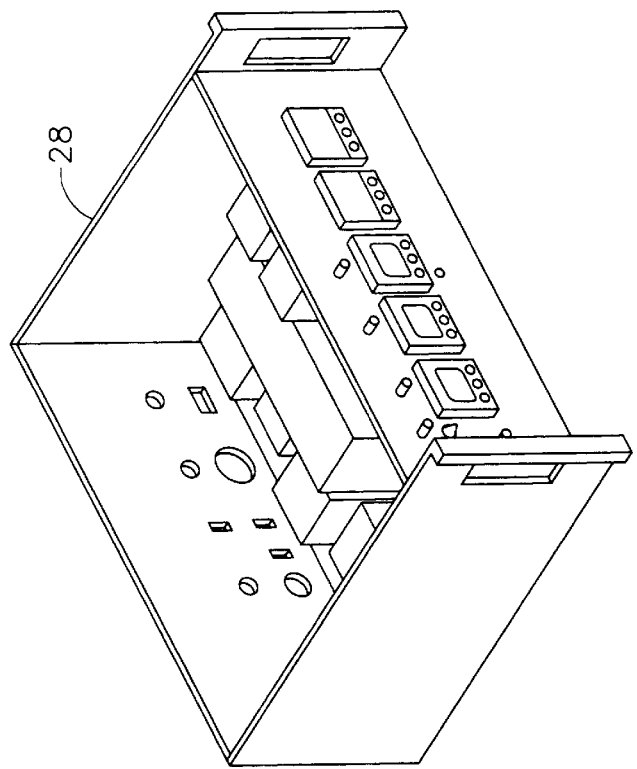
FIG. 4A shows a perspective view of the control module.
Figure 4C:
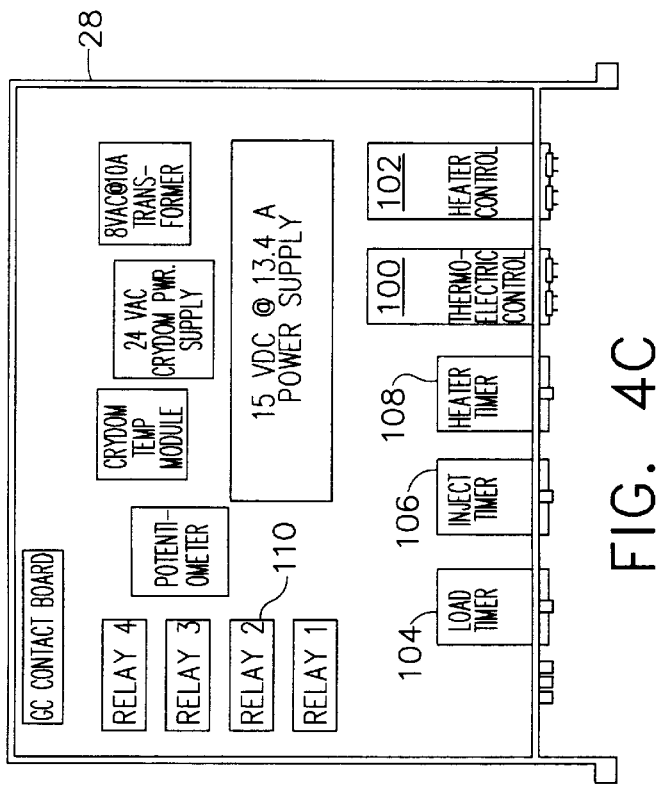
FIG. 4C shows a cut-away top view of the control module.
Figure 4B:
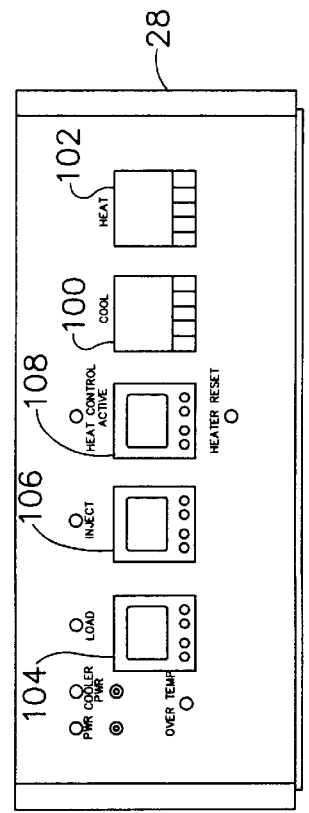
FIG. 4B shows a side view of the control module.

The thermoelectric cold trap 10 includes three key components. The first is the cold trap module 16. The second is an adsorbent tube/heater assembly 22. The third is the control module 28, shown in FIGS. 4A, 4B, and 4C, which controls the operation of the cold trap 10.

Figure 12:
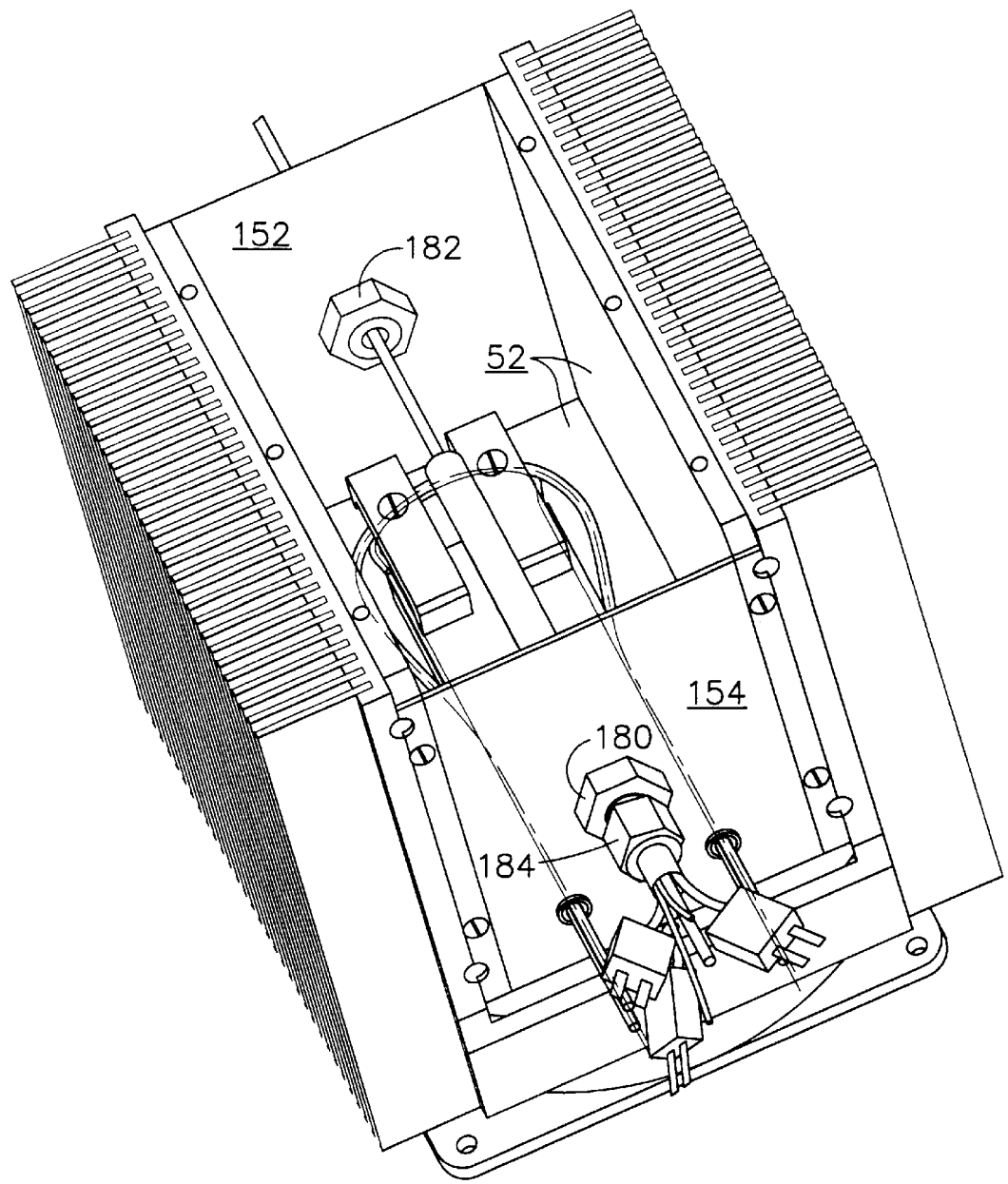
FIG. 12 shows a perspective view of a stage of assembly of the thermoelectric cold trap.

The module 16 of the cold trap 10 includes a heat exchanger 34, first and second thermoelectric modules 40,42, a cold block 46, and insulation material 52 (as shown in FIG. 12). The heat exchanger 34 preferably is a finned, U-channeled, hot side heat exchanger. The U-channel heat exchanger 34 configuration is intended to maximize the heat exchanger 34 size to improve efficiency without increasing the overall cold trap 10 size. With the addition of a cooling fan 58, the overall dimensions of the module 16 are preferably in the range of 15.2×15.2×17.8 cm (6"×6"×7"), which allows the module 16 to be moved easily and removably installed on existing GC units. These dimensions provide a balance between portability and heat exchange capacity, but modules having different dimensions also may be used.

The module 16 preferably contains two thermoelectric modules 40,42 that are connected in parallel, although a single thermoelectric module 40 could be used depending on its performance and required operating conditions such as hot and cold set point temperature and cycle times. Thermoelectric modules 40,42 are small, solid-state heat pumps, typically ranging in size from approximately 1.0 square cm to over 5.0 square cm. The thermoelectric modules 40,42 move heat from one area to another, thus creating a temperature differential. The thermoelectric modules 40,42 are made up of an array of semiconductor couples connected electrically in series and thermally in parallel. When a DC potential is applied, heat is adsorbed at one side of the thermoelectric modules 40,42, cooling that side, while heat is ejected at the other side, causing the temperature on the other side to rise. This phenomenon is known as the Peltier effect. These thermoelectric modules 40,42 preferably are commercially available units, such as Melcor Corporation model number 2SC055045-127-63L.

Two such thermoelectric modules 40,42 are presently necessary for extended operation for periods of time greater than 10 minutes at 300° C. With the two thermoelectric modules 40,42 and the U-channel heat exchanger 34, sufficient heat is removed from the cold block 46 during the cold trap 10 heating period so that the thermoelectric modules 40,42 never exceed the manufacturer's recommended maximum temperature, which is approximately on the order of 80° C. In a preferred embodiment, the minimum operating temperature of the cold trap 10 is approximately −45° C. The time required to heat the cold trap 10 to 300° C. is approximately 20 seconds. The time required to cool the cold trap 10 from 300° C. to −30° C. is approximately 5.0 minutes.

Figure 2B:
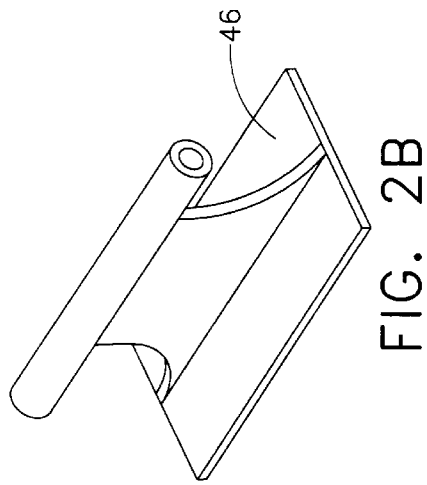
FIG. 2B shows a perspective view of the cold block.
Figure 2A:
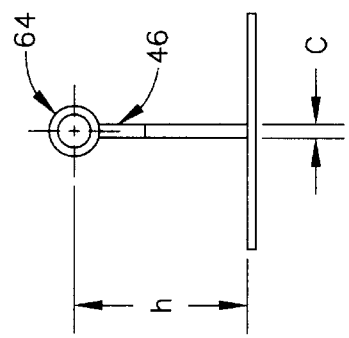
FIG. 2A shows a front view of a cold block according to the present invention.
Figure 2D:
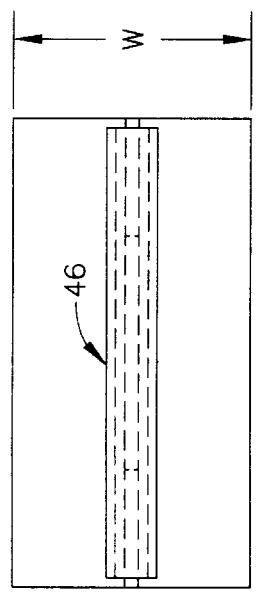
FIG. 2D shows a top view of the cold block.
Figure 2C:
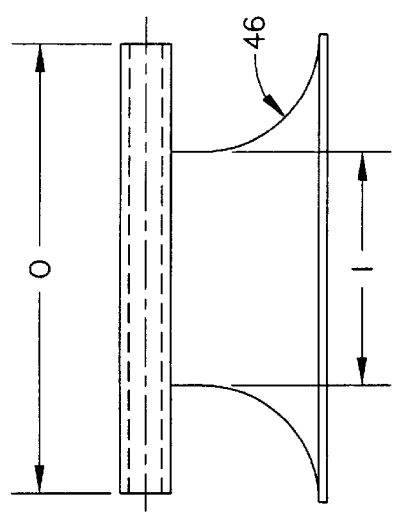
FIG. 2C shows a side view of the cold block.

The cold block 46 is a "stand-off" block which increases insulation between the cold and hot regions of the thermoelectric modules 40,42. Preferably, the cold block 46 is an aluminum "T" shape that has a very small thermal mass. FIG. 2A shows a front view of the cold block 46. The cold block 46 includes a cylinder 64 for receiving and holding the adsorbent tube/heater assembly 22. FIG. 2B shows a perspective view of the cold block 46. FIG. 2C shows a side view of the cold block 46. FIG. 2D shows a top view of the cold block 46. The cold block 46 preferably has a height h of 1.200 inches, a central thickness c of 0.075 inch, a central length l of 1.575 inches, an overall length o of 3.000 inches, and a width w of 1.575 inches when used in a cold trap 10 having the dimensions given above.

Figure 3:
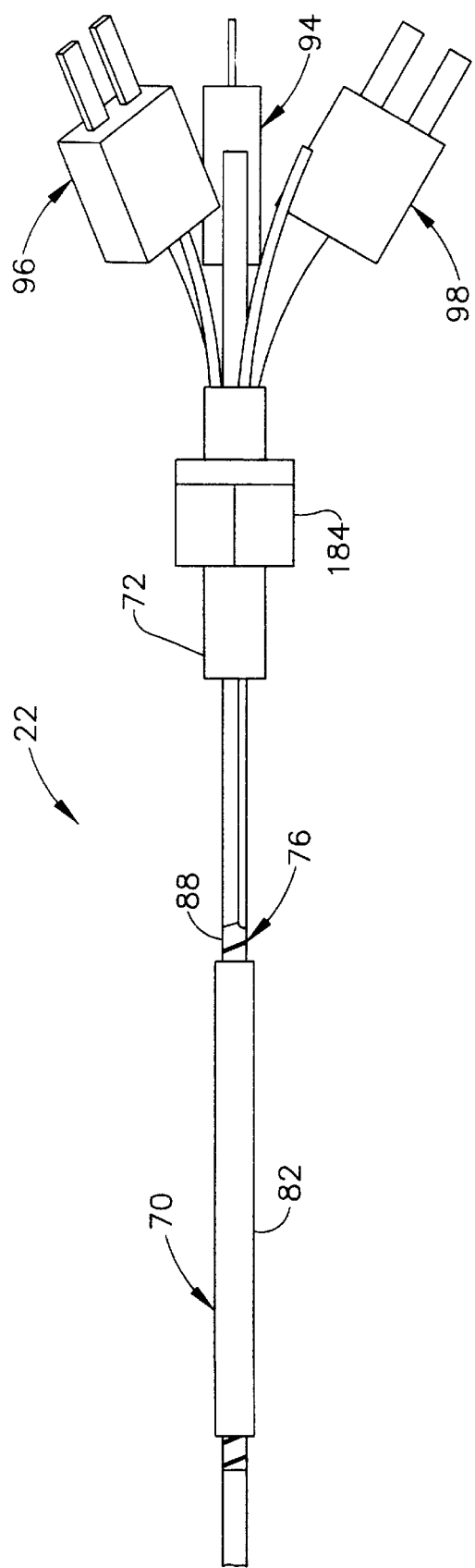
FIG. 3 shows a side view of the adsorbent tube and heater.

FIG. 3 shows a detailed view of the adsorbent tube/heater assembly 22. The adsorbent tube/heater assembly 22 includes an adsorbent tube 70 and a heater element 76 wrapped around the adsorbent tube 70 to provide approximately a 3.0 inch heated zone.

The heater may be a spiral wound metal ribbon heating element. Such a heater may be constructed from a nichrome ribbon (approximately 0.007 inches thick by 0.125 inches wide) wound around a 0.125 inch diameter spindle nineteen times to produce a heating element about 2.95 inches long. The element is removed from the spindle and one end is squared by cutting. A lead wire is brazed (silver soldered) to the other end of the element. The resultant heater is about 2.90 inches long and has an electrical resistance of 0.95±0.05 ohms.

The adsorbent tube 70 is preferably a commercially manufactured, quartz-lined or fused silica-lined, stainless steel tube with an outer diameter of about 3.2 mm (0.125") and a length of about 46 cm (18"). The adsorbent tube 70 is packed with one or more adsorbents for collecting VOCs before analysis.

The center 82 of the exterior of adsorbent tube 70 is preferably treated to remove surface contaminants and provide a good surface for attachment of thermocouples 94,96, 98. For example, the tube surface may be sanded with a 1200 grit silicone oxide sandpaper or equivalent to remove any oxide and then cleaned with acetone or another suitable solvent to remove any residual oils.

A piece of glass tape 88 approximately 0.5 inches wide and 3 inches long is centered and secured along the axis of the adsorbent tube. Three type "K" thermocouples 94,96,98 are centered on the adsorbent tube 70 and are laid side-by-side against the tube 70 surface. The glass tape 88 is then rolled around the adsorbent tube 70, securing the three thermocouples 94,96,98 in place.

The nichrome heater element is slid over the glass tape containing the thermocouples and the square cut end is secured to the stainless steel tube by spot welding. Tension is applied to the spiral heating element, causing it to tighten about the tube. A piece of glass tape is placed on the heater element to hold it in place and provide electrical insulation. A ground connection is provided on the tube by rolling another piece of nichrome ribbon (generally less than about 0.375 inches long ) around the tube and welding it along its entire length. A second lead wire is brazed to this ground connection.

Glass tape or other suitable material is used to insulate the heater's electrical connection and isolate it from the tube. Care must be taken to ensure complete electrical isolation of the heater element and maintain the desired resistance of about 0.95±0.05 ohms in the finished tube assembly.

The adsorbent tube 70 and its heater element 76 are secured within a locator tube 72 to assist in positioning them within the cold block 46. A locator tube 72 and Swagelok® nut assembly 184 are slid over the insulated heater 76 and lead wires and the adsorbent tube 70 is inserted into an assembly fixture to position the nut 184 relative to the cold block 46. The locator tube 72 and nut 184 are secured in place and the adsorbent tube 70 is bottomed against the jig. Quick setting epoxy or another suitable material is placed in the locator tube 72 to secure the adsorbent tube 70 in its desired position. When the epoxy has cured, the tube 70 may be removed from the assembly fixture. If desired, additional epoxy may be added inside the locator tube 72 to ensure a hermetic seal.

The cold trap may accommodate removable and replaceable adsorbent tubes to minimize equipment setup time when tubes with different adsorbents are used. To facilitate the insertion and removal of different tubes and reduce the risk to damage to the heater element 76 and associated thermocouples 94,96,98, the heater 76 and thermocouples 94,96,98 may be fixed to the cold block 46 rather than provided on each adsorbent tube 70.

Figure 5A:
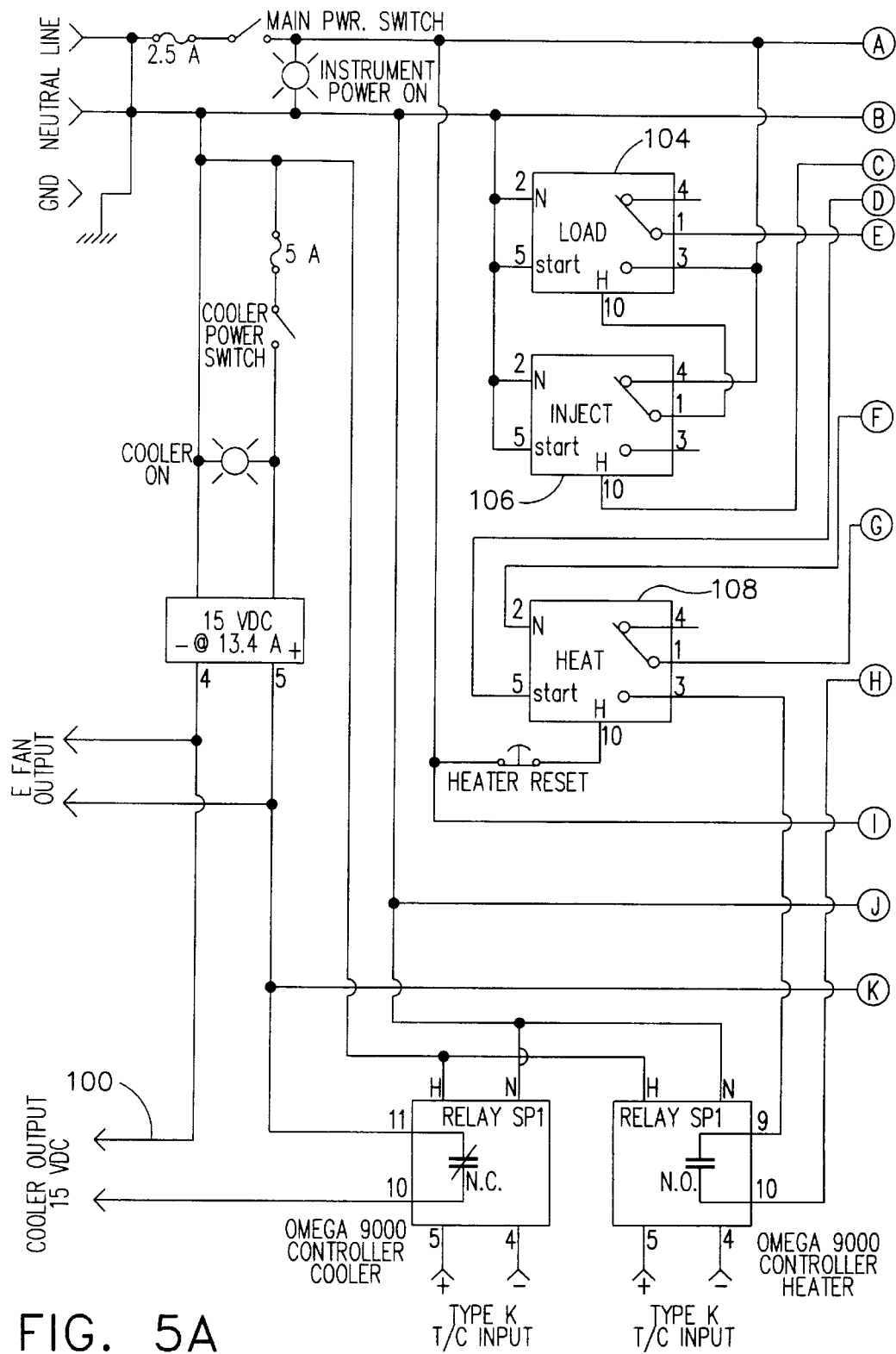
FIG. 5 shows a wiring schematic of the control module.
Figure 5B:
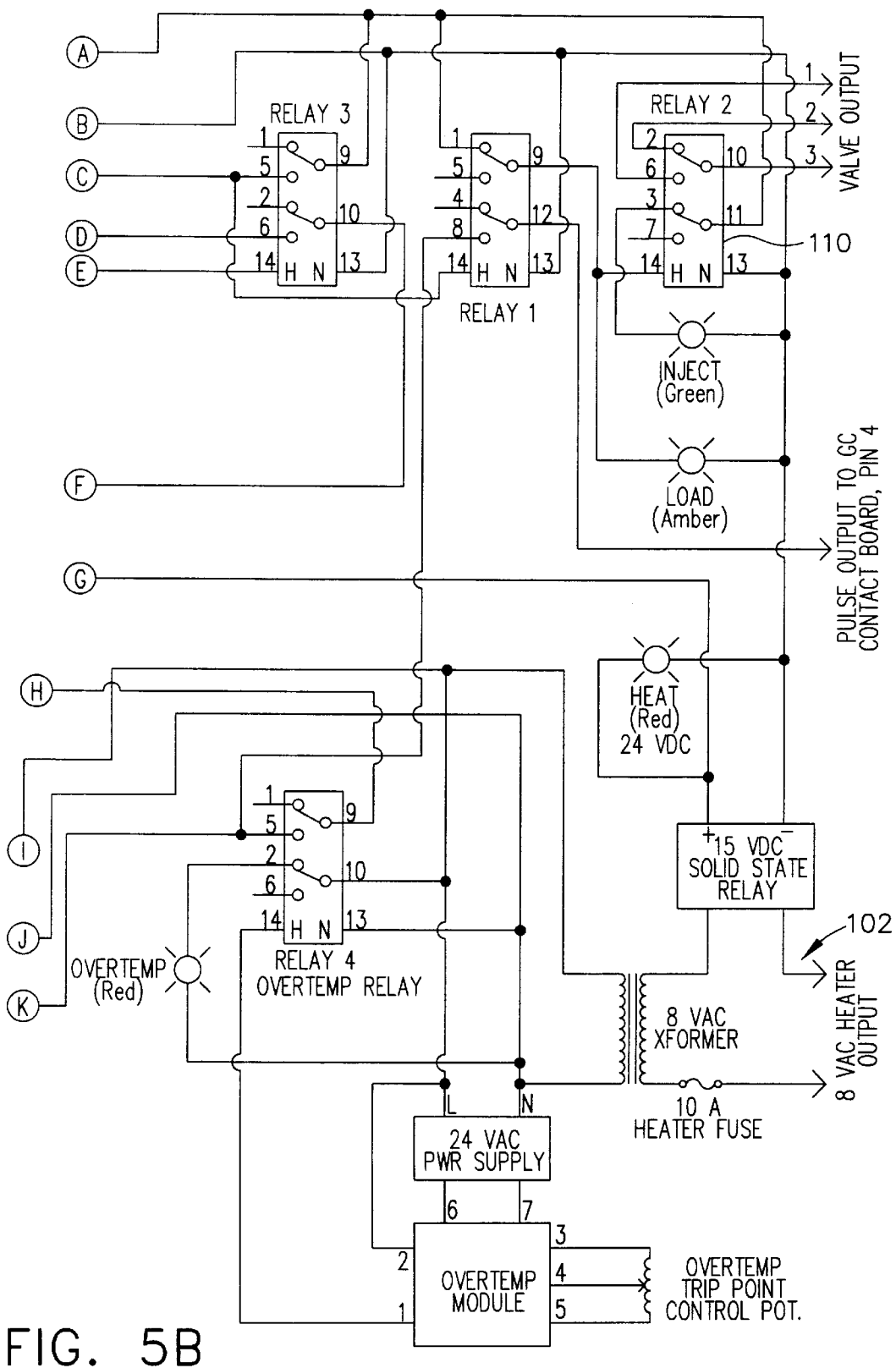

With continuing reference to FIGS. 1 and 3, FIGS. 4A, 4B, and 4C show the control module 28, and FIG. 5 shows a wiring schematic of control module 28 used with the system. The control module 28 supplies power to the thermoelectric modules 40,42 and to the heating element 76, thereby controlling the cold and hot points using individual temperature controllers 100,102. The control module 28 also includes timing circuitry, such as timers 104,106,108 to set the periods for the cold and hot cycles. The timers 104,106, 108 preferably are commercially available and well-known in the art.

Figure 14A:
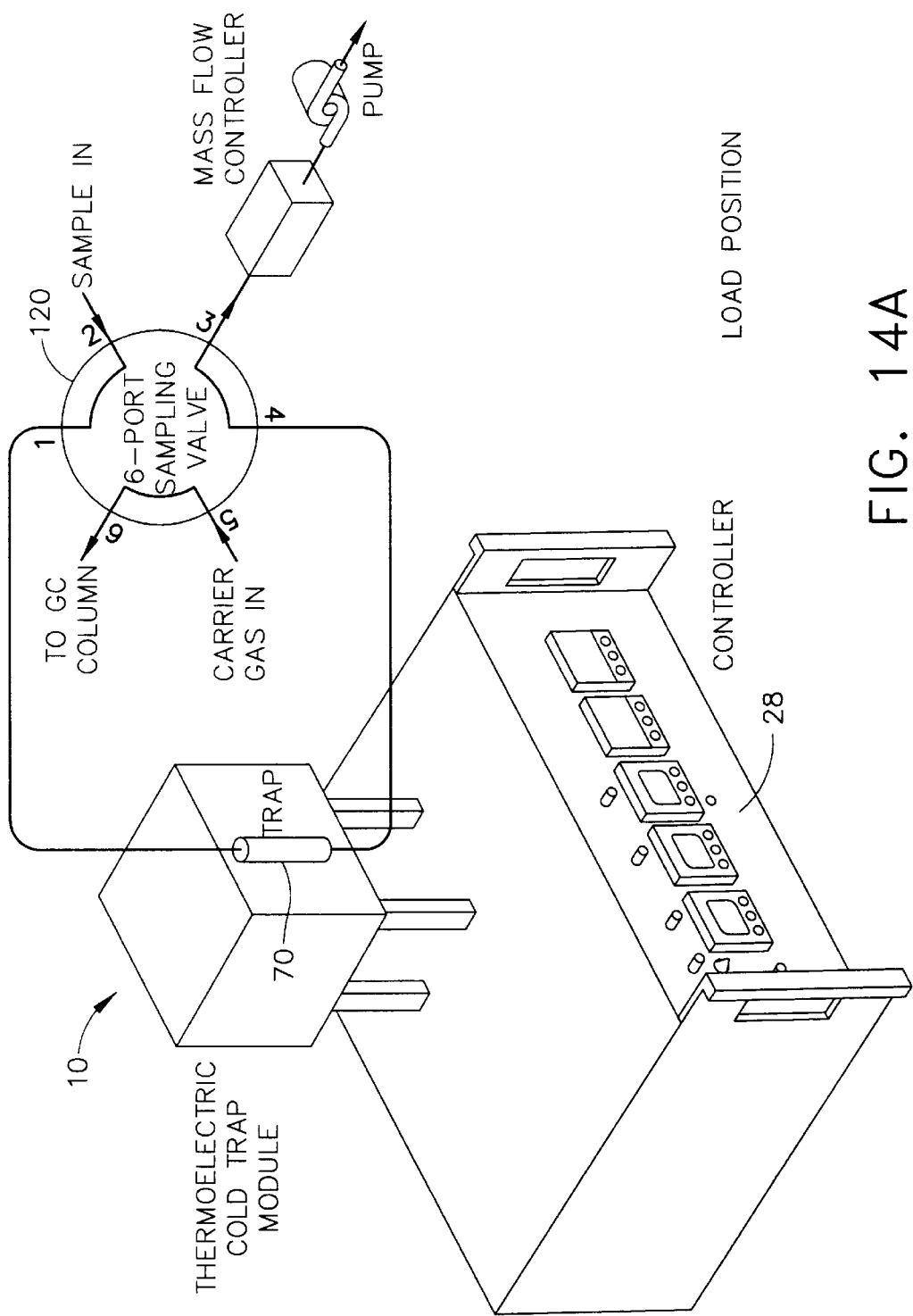
FIG. 14A shows a six-port valve of a gas chromatograph in the load position.
Figure 14B:
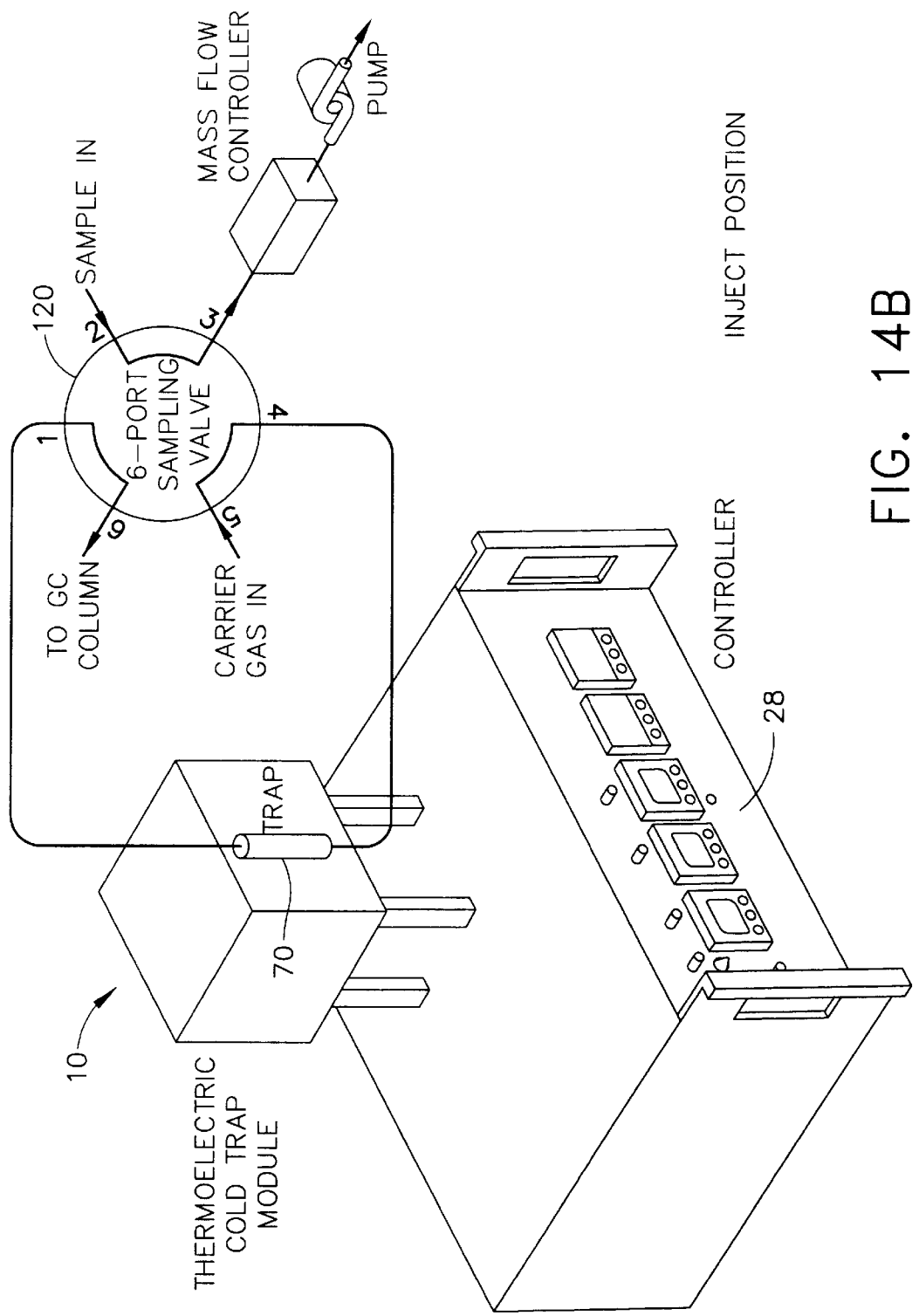
FIG. 14B shows the six-port valve of a gas chromatograph in the inject position.

The cold trap 10 may include an adapter, not shown in the drawings, to connect the cold trap 10 to any GC using a six port valve 120, shown in FIGS. 14A and 14B. FIG. 14A shows the valve 120 in the load position and FIG. 14B shows the valve 120 in the inject position. The control module 28 may include relays 110 and contact closure circuitry 114 that interface with the timing circuitry to operate the gas chromatograph ("GC") valve 120, and to start the GC and any associated data acquisition systems. The valve 120 remains in the load position while the sample is being collected and cooled and is switched to the inject position when sample desorption by heating begins.

With the controller in the idle mode, the cold temperature controller 100 is operational. When the cold temperature controller 100 is switched to the operate mode, the timers 104,106,108 are functional. When the first timer 104 is activated, a relay 110 is activated and a signal is sent to turn the GC valve 120 to the load position. The first timer 104 determines the length of time that the GC valve 120 will be in the load position (sample collection mode). The second and third timers 106,108 are started upon completion of the cycle by the first timer 104. Activation of the second timer 106 triggers the GC valve 120 to switch to the sample inject position (via a momentary contact closure signal). The second timer 106 is operational for the entire GC run cycle. The third timer 108, which starts simultaneously with the second timer 106, determines the length of time that the heater element 76 is activated.

A typical GC operational cycle is 30 minutes, although the cycle time may vary depending on the amount of time needed to chromatographically resolve the compounds of interest. For complex mixtures of compounds like those identified by the U.S. EPA as "TO-14 compounds," for example, the full GC cycle time of 30 minutes is needed. If the GC run time includes the valve 120 load time of five minutes and the trap heating time of two minutes, then a total cycle time of 37 minutes is required. The minimum cycle time is determined by the load time, the heat time, and the transient time (the time required to reach the cold set point after attaining the hot set point temperature), which is approximately 10 minutes.

Figure 6:
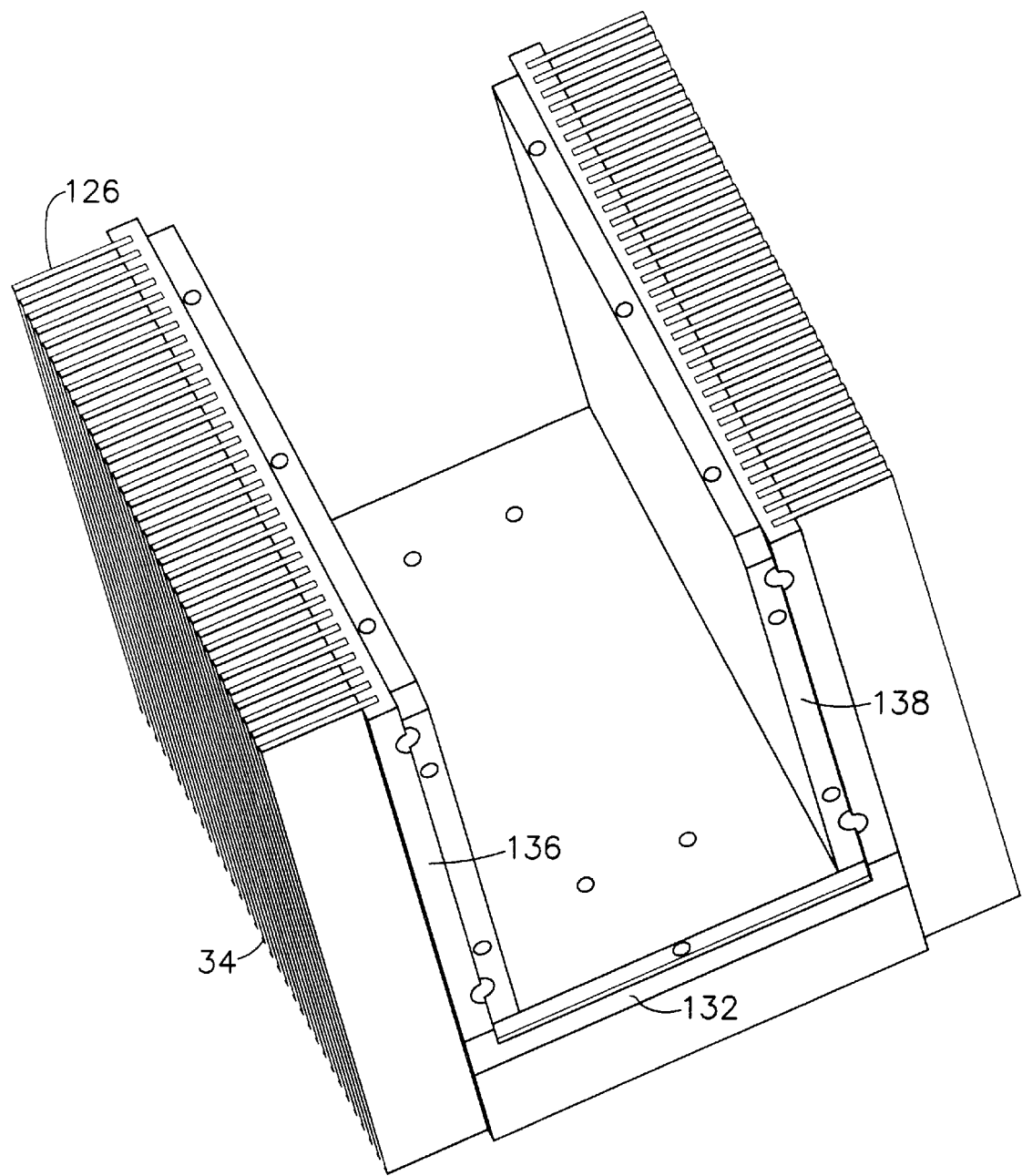
FIG. 6 shows a perspective view of a stage of assembly of the thermoelectric cold trap.
Figure 7:
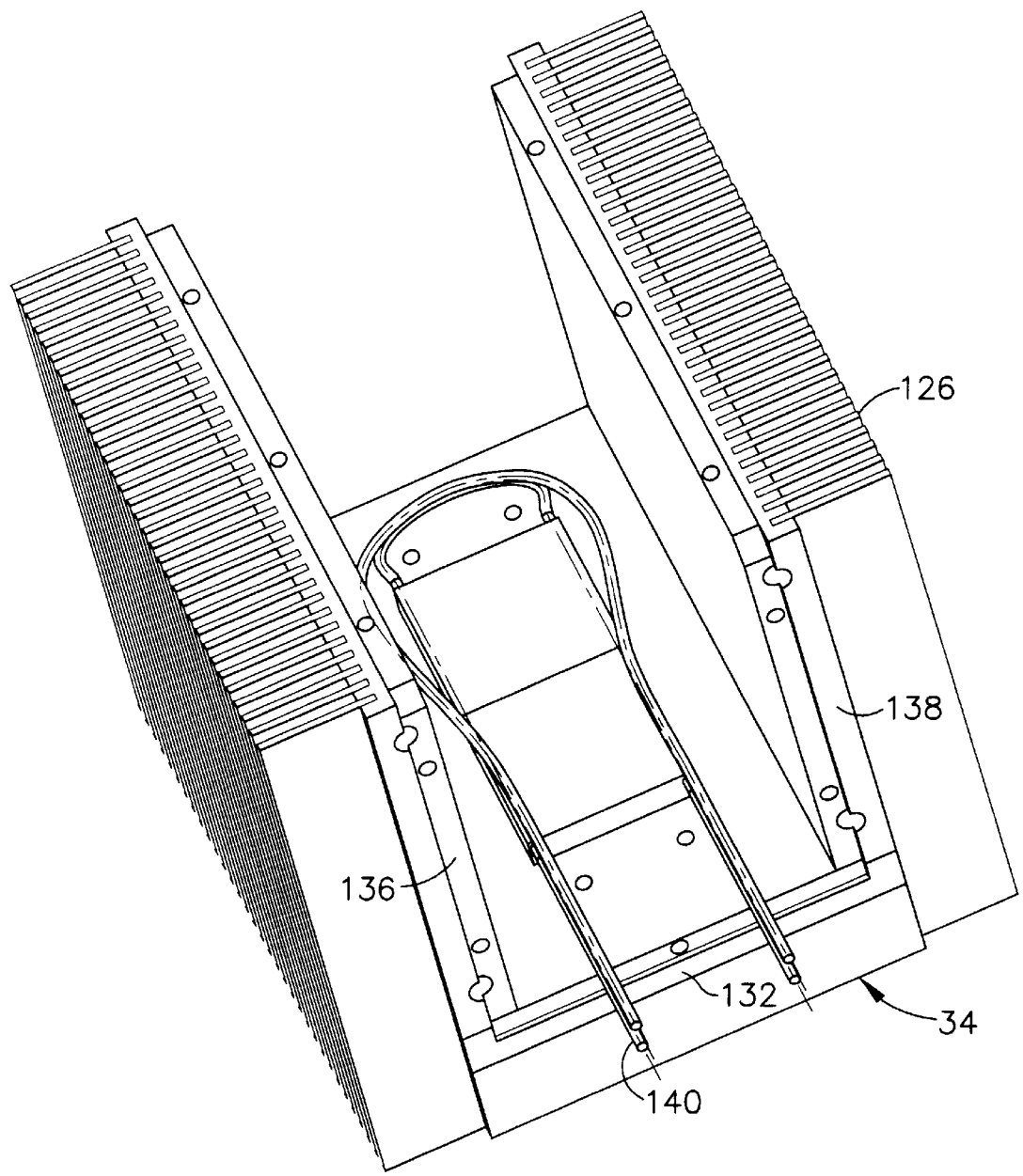
FIG. 7 shows a perspective view of a stage of assembly of the thermoelectric cold trap.

With reference to FIGS. 6–13, the preferred procedures for assembling the cold trap 10 will now be disclosed. With reference to FIG. 6, the materials for the heat exchanger 34 are prepared such that the fins 126 preferably are precut to a height of approximately 1 inch. If desired, the fins 126 could be cut or machined during the manufacturing process. In a preferred embodiment, the fins 126 are bonded in place with an epoxy. The materials of the heat exchanger 34 are then welded together in stages to prevent the epoxy from melting or burning. With reference to FIG. 7, prior to welding, the back plate 132 of the heat exchanger 34 is checked for flatness in the mounting area for the thermoelectric modules 40,42. The surface area of the back plate 132 that will contact the thermoelectric modules 40,42 should have a lapped finish. The fins 126 of the back plate 132 and side plates 136,138 preferably are aligned to minimize air-side pressure drop. The back plate 132 and side plates 136,138 are welded together in the U-shape.

Before fastening the thermoelectric modules 40,42 to the back plate 132 of the heat exchanger 34, a small amount of thermal joint compound may be applied to both the cold and hot side of the two thermoelectric modules 40,42. The thermoelectric module 40,42 are placed with their hot sides against the heat exchanger 34 and the wires 140 connected to the control module (not shown) positioned as shown in FIG. 7.

Figure 8:
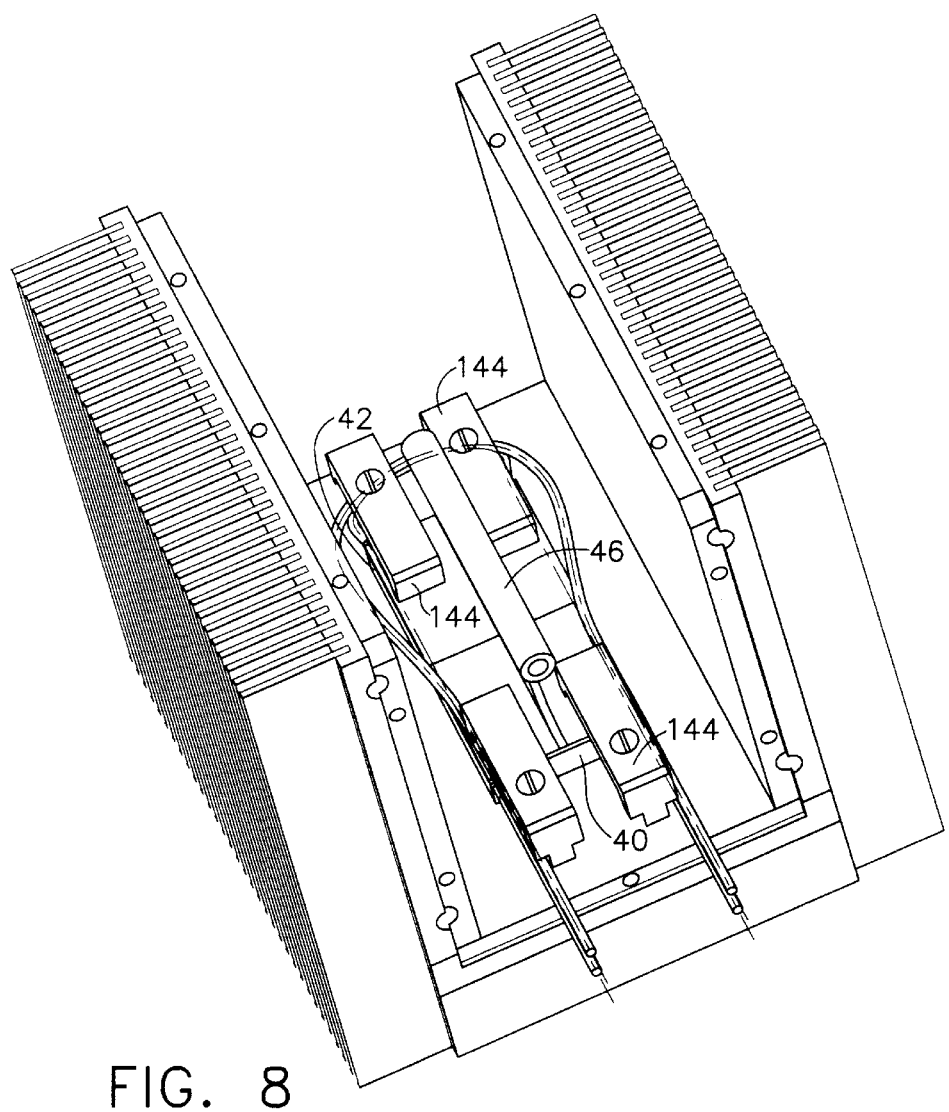
FIG. 8 shows a perspective view of a stage of assembly of the thermoelectric cold trap.
Figure 9:
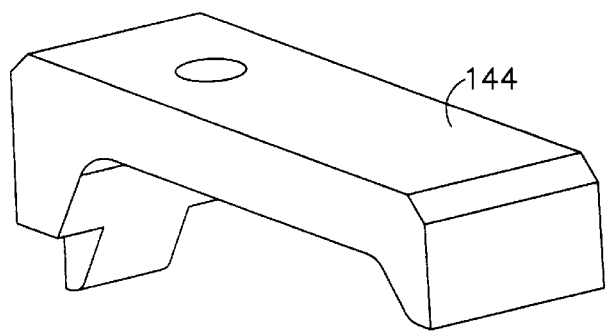
FIG. 9 shows a perspective view of a phenolic clamp.

With reference to FIG. 8, the cold block 46 and clamps, preferably phenolic clamps 144, are placed in the cold trap 10 with the cold block 46 in engagement with the cold side of thermoelectric modules 40,42. The clamps may also be formed from other heat resistant materials, or the cold block may be held in place by any other suitable clamping or holding apparatus. Alternatively, the components may be held in position during assembly by a fixture, and then secured in position by the foamed insulation. If clamps are used, the clamp should minimize thermal transfer losses while providing suitable clamping forces. A clamp 144 having the shape illustrated in FIG. 9 and made of phenolic resin or another suitable material is preferred.

The stainless steel screws of the phenolic clamps 144 are tightened to provide a snug fit and good thermal conductivity from the thermoelectric modules 40,42. Stainless steel screws are preferred to minimize thermal losses, although other suitable fasteners also may be used. Final tightening of the screws is delayed until just before filling the cold trap 10 with insulation material 52. A protective layer, such as single layer of duct tape or the like, may be placed on all four of the exposed sides of the two thermoelectric modules 40,42 before the insulation 52 is added. This protective layer preferably is used to prevent uncatalyzed liquid two-part insulation material 52 from entering the thermoelectric modules 40,42. However, if the thermoelectric modules 40,42 are sealed, the tape may not be necessary.

Figure 10:
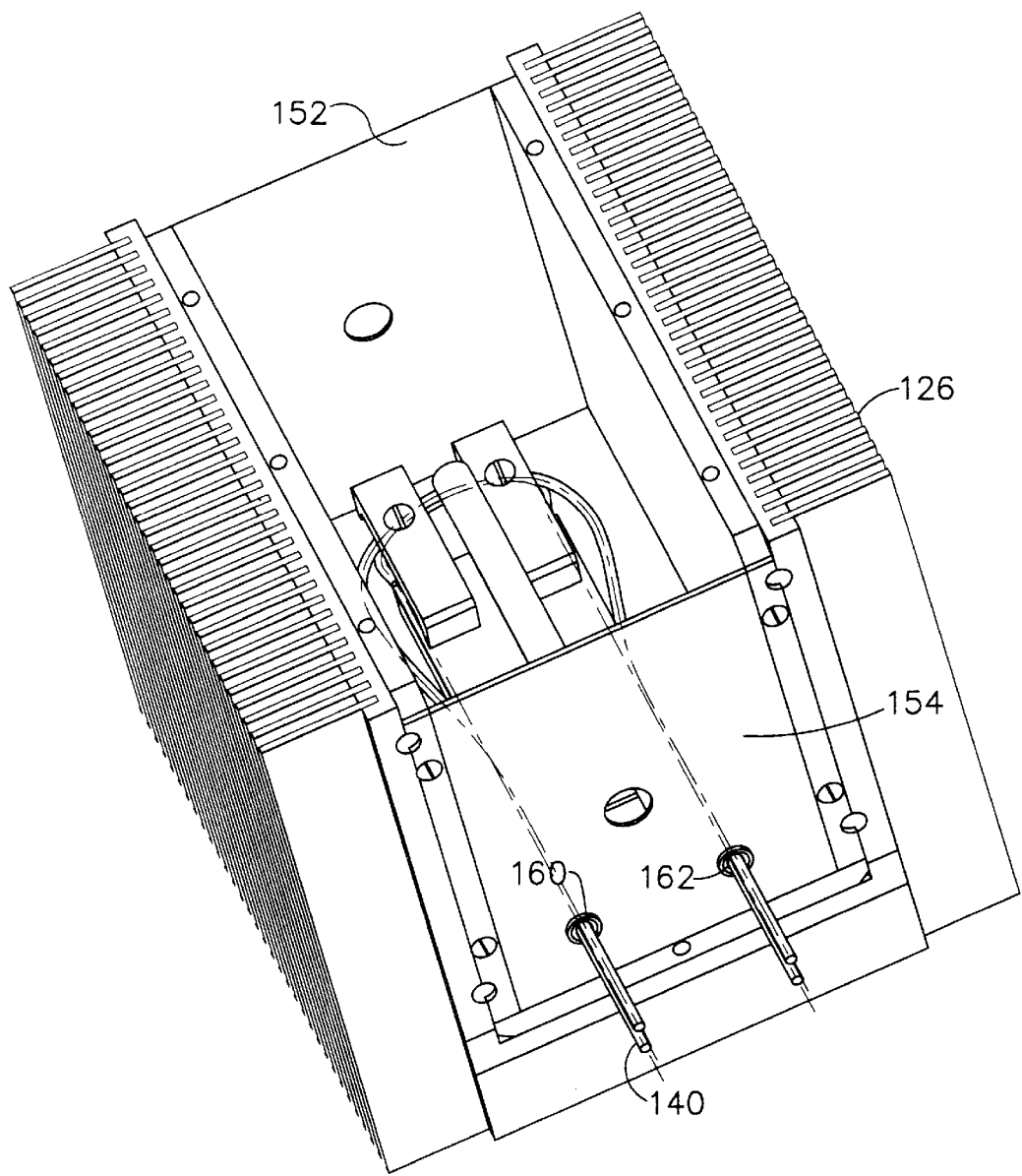
FIG. 10 shows a perspective view of a stage of assembly of the thermoelectric cold trap.
Figure 11:
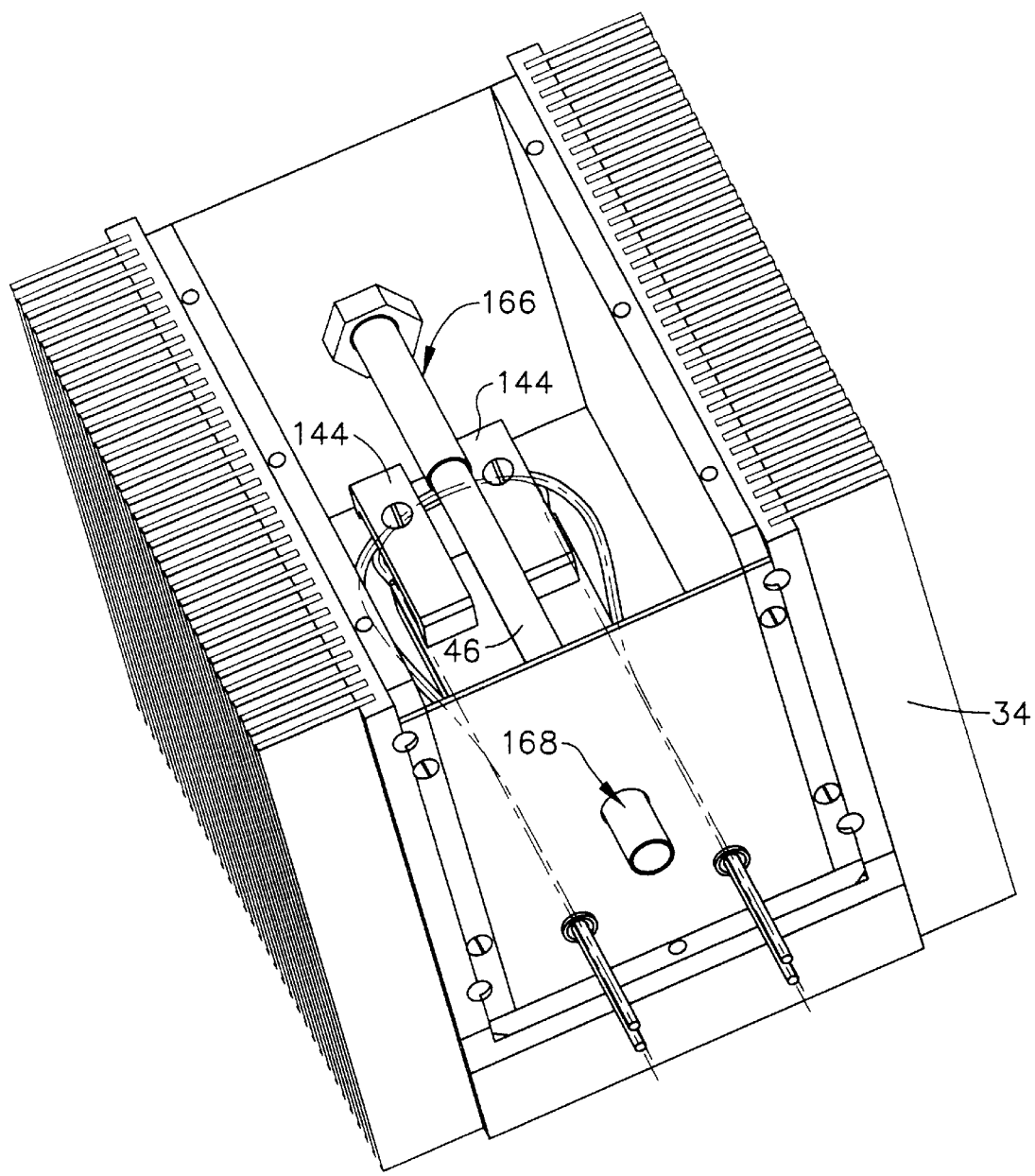
FIG. 11 shows a perspective view of a stage of assembly of the thermoelectric cold trap.

With reference to FIG. 10, during the next step of the assembly process the top cover plate 152 and bottom cover plate 154 are attached to the cold trap 10. The wiring 140 for the thermoelectric modules 40,42 may be routed through two rubber grommets 160,162 in the bottom cover plate 154. A barrier of duct tape or any other suitable material is then placed over the fins 126 to prevent insulating material (not shown) from entering the fin cavities. With reference to FIG. 11, two tubing cores 166,168 are greased with a silicone vacuum grease or equivalent material and then mounted in position to seal the cold block 46. The screws of the phenolic clamps 144 are securely tightened.

During the insulation process, a small quantity of two-part, polyurethane insulation material is mixed and prepared according to manufacturer's directions and poured evenly into the heat exchanger 34. For a heat exchanger 34 having the approximate dimensions provided above, approximately 140 cc of insulation would be required. The insulation material 52 expands to fill the heat exchanger 34. After the insulation material 52 cures, the insulation material 52 is trimmed flush with the heat exchanger fins 126 so that the front cover plate 174 can be installed. Use of expanding, polyurethane insulation is preferred because it provides effective thermal insulation and assists in stabilizing the cold trap 10 components. Other types of insulation also may be used, although foamed or other expandable insulation is preferred.

With reference to FIG. 12 and continuing reference to FIG. 11, after the insulation material 52 has cured, the two tubing cores 166,168 are removed and male connectors 180,182, preferably Swagelok® male connectors, are threaded into the nuts on the top and bottom cover plates 152,154. The front cover plate 174 and the heat exchanger fan 58 are then installed.

Figure 13:
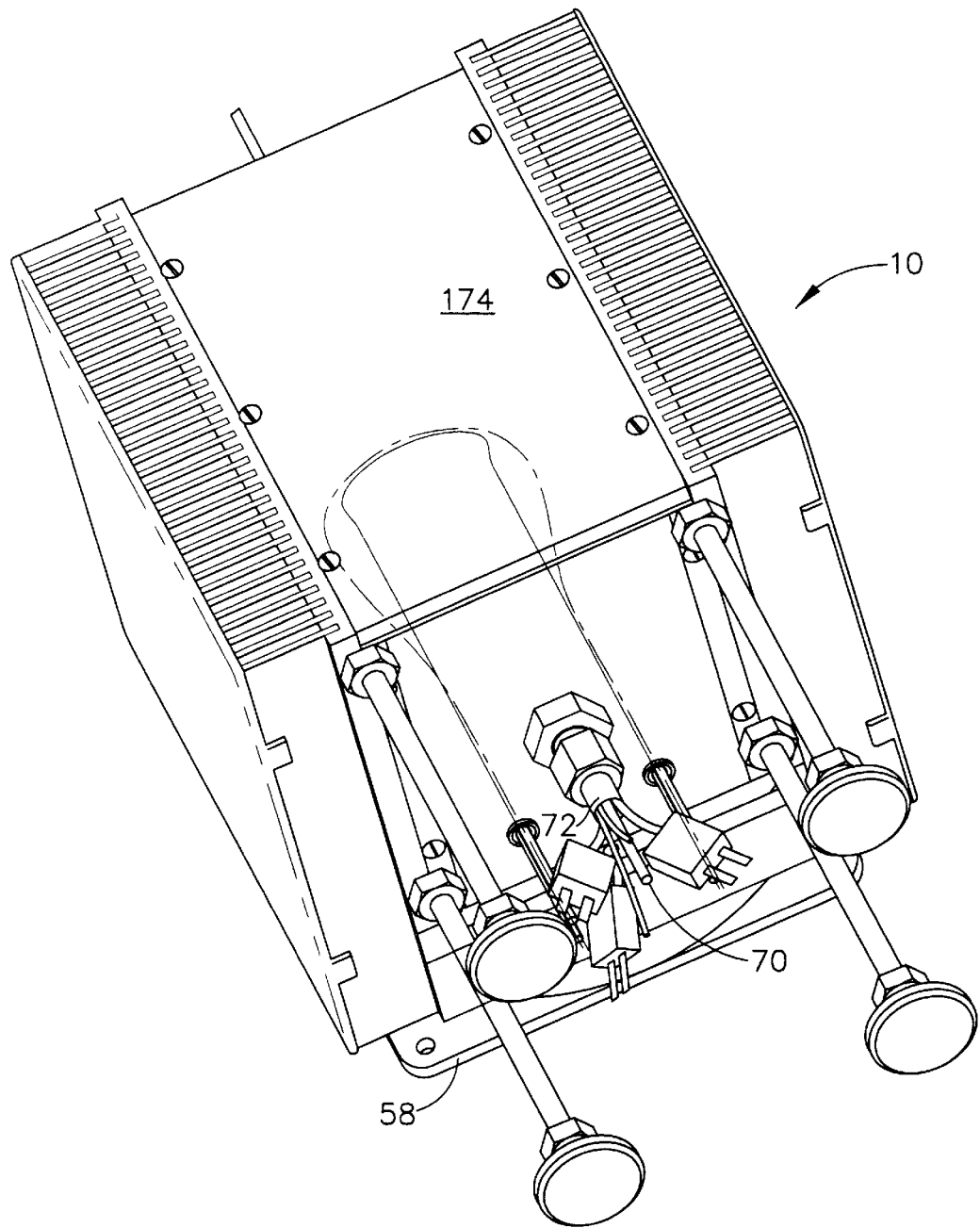
FIG. 13 shows a perspective view of the completely assembled thermoelectric cold trap.

With reference to FIG. 13, the final step of the assembly process is the installation of the adsorbent tube 70 and heater element 76 into the thermoelectric cold trap 10. As described above, the adsorbent tube 70 and its heater element 76 are placed within a locator tube 72 with a Swagelok® nut assembly 184 secured in a predetermined location. The tube assembly 22 is inserted into the bottom cover plate 154 and pushed through the void in the insulation 52 formed by the tubing cores 166,168 and the cylinder 64 of the cold block 46 until the leading end of the tube assembly 22 extends through the Swagelok® connector 182 on the top cover plate 152 and the Swagelok® nut 184 on the locator tube 72 engages the mating Swagelok® connector 180 on the bottom cover plate 154. The lead wires of the heater 76 are then connected to the control module 28.

The thermoelectric cold trap 10 may be assembled with a new gas chromatograph, or the thermoelectric cold trap 10 may be retrofitted by any suitable means to an existing gas chromatograph.

unit and (2) a Thomas dual diaphragm pump. The sample flow rate was controlled at 20 cc/min with a collection (load) time of five minutes, resulting in a sample volume of 100 $cm^3$. The trap was installed so that during sample adsorption at −30° C., sample flow was directed initially though the Carbopack B adsorbent and then through the Carbosieve S-III adsorbent. During thermal desorption at 250° C., the condensed VOCs were backflushed off the trap. The trap was connected to a 2-position Valco six-port valve, which in turn was interfaced to the Varian GC.

Collection/recovery efficiencies were determined using experimentally measured sample loop (1.18 $cm^3$) and cold trap (104 $cm^3$) volumes. These results are shown in Table 1:

TABLE 1

COLLECTION/RECOVERY EFFICIENCIES FOR TARGET COMPOUNDS

| | | Peak Areas | | | % Recovered | | |
|---|---|---|---|---|---|---|---|
| Compound | Loop | Trap Run #1 | Trap Run #2 | Trap Run #3 | Trap #1 | Trap #2 | Trap #3 |
| ethane | 19520 | 21554 | 32549 | 59138 | 95 | 100 | 98 |
| ethylene | 21567 | 26394 | 36509 | 66517 | 105 | 101 | 100 |
| propane | 31725 | 37165 | 54154 | 98953 | 101 | 102 | 101 |
| propylene | 32541 | 40751 | 57118 | 103562 | 108 | 105 | 103 |
| isobutane | 43633 | 51167 | 74090 | 136053 | 101 | 102 | 101 |
| n-butane | 39248 | 45053 | 66295 | 122414 | 99 | 101 | 101 |
| acetylene | 19694 | 20441 | 32084 | 59845 | 89 | 97 | 99 |
| dilution factor→ | | 0.0132 | 0.019 | 0.035 | | | |
| enrichment factor→ | | 88 | 88 | 88 | | | |

Chemical testing was carried out with a target set of seven volatile organic compounds including the common $C_2$ through $C_4$ hydrocarbons (e.g., ethane, ethylene, and acetylene). These compounds were targeted because they are very volatile and therefore are difficult to capture with a preconcentration cold trap system. These compounds are also ubiquitous in the atmosphere and are key compounds on the United States Environmental Protection Agency's list of ozone precursors.

The cold trap was tested with a Varian 3600 GC equipped with a flame ionization detector. The detector output signal was connected to a personal computer running ChromPerfect GC software.

Separation was accomplished using an aluminum oxide PLOT capillary column (Chrompack) having a length of 50 m and an interior diameter of 0.32 mm. The GC oven was temperature programmed from −30° C. to 120° C., with an initial hold of two minutes and a ramp of 15 degrees C per minute. The carrier gas was zero grade nitrogen with a flow rate of 4 $cm^3$/min. The flame ionization gases were ultra zero air (300 $cm^3$/min) and ultra zero hydrogen (30 $cm^3$/min).

The adsorbent trap was a fused silica lined stainless steel tube having a length of 25 cm and an interior diameter of 0.2 cm that was packed sequentially with two adsorbents. The first adsorbent was ~0.02 g (2 cm long) of Carbopack B (60/80 mesh) and the second adsorbent was ~0.02 g (1 cm long) of Carbosieve S-III (60–80 mesh).

Sample flow through the trap was controlled using (1) a Sierra Instrument Model 810 mass flow controller/readout The loop area response is that amount measured when the sample loop is challenged with an undiluted mixture of the seven targeted compounds (nominally 1 ppm±10%). The trap area response results were obtained by challenging the cold trap with diluted levels of the same gas mixture. The percent recovered is determined by the measure trap/loop ratio divided by the product of the dilution factor and the enrichment factor, where the dilution factor is $$\text{dilution factor} = \frac{\text{calibration gas flow}}{\text{zero air flow plus calibration gas flow}}$$

and the enrichment factor is $$\text{enrichment factor} = \frac{\text{cold trap collection volume}}{\text{sample loop volume}}$$

As shown in Table 1, experimental results showed excellent recoveries (100±4%) using the cold trap 10.

The preferred embodiments have been described above. It will be apparent to those skilled in the art that the above methods may incorporate changes and modifications without departing from the general scope of this invention. It is intended to include all such modifications and alterations in so far as they come within the scope of the appended claims or the equivalents thereof.

Having thus described the invention, it is now claimed:

1. A thermoelectric cold trap for collecting a gas sample for analysis, comprising:

a U-shaped heat exchanger having a base;

a thermoelectric module having a hot side and a cold side, said hot side engaging said base;

a T-shaped cold block engaging said cold side of said thermoelectric module and having a cylinder for removably receiving a sample collection tube/heater assembly; and a control module electrically connected to said thermoelectric module, said control module selectively actuating said thermoelectric module to cool a sample collection tube received in said cylinder.

2. The thermoelectric cold trap of claim 1, further comprising:

a second thermoelectric module engaging said base and coupled in parallel to said first thermoelectric module.

3. The thermoelectric cold trap of claim 1, further comprising:

foamed insulation around said cold block.

4. A thermoelectric cold trap for collecting a gas sample for analysis, comprising:

a U-shaped heat exchanger having a base;

a thermoelectric module having a hot side and a cold side, said hot side engaging said base;

a cold block engaging said cold side of said thermoelectric module and having a holder for removably receiving a sample collection tube containing an adsorbent;

a heater communicating with a sample collection tube received in said holder; and a control module electrically connected to said heater and said thermoelectric module, said control module selectively actuating said heater and said thermoelectric module to heat and cool a sample collection tube received in said holder.

5. The thermoelectric cold trap of claim 4, wherein said heat exchanger is finned.

6. The thermoelectric cold trap of claim 4, wherein said cold block is T-shaped.

7. The thermoelectric cold trap of claim 4, wherein said holder comprises a cylinder formed integrally with said cold block.

8. The thermoelectric cold trap of claim 4, wherein said cold block is aluminum.

9. The thermoelectric cold trap of claim 4, further including a clamp holding said base, said thermoelectric module, and said cold block together.

10. The thermoelectric cold trap of claim 9, wherein said clamp is a phenolic clamp.

11. The thermoelectric cold trap of claim 4, further comprising a second thermoelectric module engaging said base.

12. The thermoelectric cold trap of claim 11, wherein said first thermoelectric module and said second thermoelectric module are connected in parallel.

13. The thermoelectric cold trap of claim 4, further comprising:

an adapter for connecting said thermoelectric cold trap to a gas chromatograph.

14. The thermoelectric cold trap of claim 4, further comprising:

foamed insulation shielding said cold block.

15. The thermoelectric cold trap of claim 14, wherein said insulation comprises polyurethane foam insulation.

16. The thermoelectric cold trap of claim 4, wherein said U-shaped heat exchanger further comprises:

first and second side plates connected to said base and extending from opposite edges of said base.

17. The thermoelectric cold trap of claim 4, wherein the control module further comprises timing circuitry for setting periods of hot and cold cycles and temperature controllers for controlling temperature of said heater and said thermoelectric module.

18. An apparatus for preconcentrating gaseous species for analytical detection, comprising:

a U-shaped heat exchanger having a base;

a thermoelectric module having a hot side and a cold side, said hot side engaging said base;

a T-shaped cold block engaging said cold side of said thermoelectric module and having a holder for engaging a sample collection tube;

a sample collection tube containing an adsorbent, said sample collection tube being removably receivable within said holder;

a heater for heating said sample collection tube received within said holder; and a control module electrically connected to said heater and said thermoelectric module, said control module selectively actuating said heater and said thermoelectric module to heat and cool said sample collection tube.

19. The apparatus of claim 18, further comprising:

a second thermoelectric module engaging said base and connected in parallel to said first thermoelectric module.

20. The apparatus of claim 18, further comprising:

foamed insulation shielding said cold block and said adsorbent tube.

21. The apparatus of claim 18, wherein said control module further comprises timing circuitry for setting periods of hot and cold cycles and temperature controllers for controlling temperature of said heater and said thermoelectric module.

22. A method of assembling a thermoelectric cold trap for collection of gas samples for analysis, said method comprising the steps of:

providing a U-shaped heat exchanger;

fastening a thermoelectric module having a hot and a cold side to said heat exchanger with said hot side positioned against said heat exchanger;

securing a cold block to said cold side of said thermoelectric module;

providing a sample collection tube holder in engagement with said cold block; and electrically connecting a control module to said thermoelectric module for selectively actuating said thermoelectric module to cool a sample collection tube received in said holder.

23. A method of collecting volatile compounds from gas samples, comprising the steps of:

providing a U-shaped heat exchanger;

fastening a thermoelectric module having a hot side and a cold side to said heat exchanger with said hot side positioned against said heat exchanger;

providing a cold block having a holder for engaging a gas sample collection tube;

securing said cold block to said cold side of said thermoelectric module;

inserting a gas sample collection tube containing an adsorbent within said holder;

providing a heater in communication with said sample collection tube;

electrically connecting a control module to said thermoelectric module and said heater;

passing a gas sample through said adsorbent tube received within said holder;

causing said control module to actuate said thermoelectric module to cool said adsorbent tube and condense sample components;

causing said control module to actuate said heater to desorb the condensed sample components.

* * * * *

UNITED STATES PATENT AND TRADEMARK OFFICE
CERTIFICATE OF CORRECTION

PATENT NO. : 6,076,357
DATED : June 20, 2000
INVENTOR(S) : Michael W. Holdren, et al.

It is certified that error appears in the above-identified patent and that said Letters Patent is hereby corrected as shown below:

The Assignee name should be spelled Battelle Memorial Institute (it is incorrectly spelled as Battele Memorial Institute on the issued Patent).

<u>Column 2,</u>
Line 34, BACKGROUND OF THE INVENTION, the word "sample" is incorrectly typed as "sampe."

Signed and Sealed this

Third Day of July, 2001

*Attest:*

*Attesting Officer*

NICHOLAS P. GODICI
*Acting Director of the United States Patent and Trademark Office*